(12) United States Patent
Sagae

(10) Patent No.: US 7,012,150 B2
(45) Date of Patent: Mar. 14, 2006

(54) METHOD OF MANUFACTURING BIS(CYCLOPENTADIENLY)RUTHENIUM AND BIS(CYCLOPENTADIENYL)RUTHENIUM MANUFACTURED BY THE SAME

(75) Inventor: Takeyuki Sagae, Hiratsuka (JP)

(73) Assignee: Tanaka Kikinzoku Kogyo K.K., Tokyo (JP)

(*) Notice: Subject to any disclaimer, the term of this patent is extended or adjusted under 35 U.S.C. 154(b) by 137 days.

(21) Appl. No.: 10/491,125

(22) PCT Filed: Aug. 4, 2003

(86) PCT No.: PCT/JP03/09860

§ 371 (c)(1),
(2), (4) Date: Mar. 29, 2004

(87) PCT Pub. No.: WO2004/013150

PCT Pub. Date: Feb. 12, 2004

(65) Prior Publication Data

US 2004/0260109 A1 Dec. 23, 2004

(30) Foreign Application Priority Data

Aug. 5, 2002 (JP) .................................... 2002-227084

(51) Int. Cl.
*C07F 17/02* (2006.01)

(52) U.S. Cl. ..................................................... 556/136
(58) Field of Classification Search .................. 556/136
See application file for complete search history.

(56) References Cited

U.S. PATENT DOCUMENTS

| 5,641,871 | A | 6/1997 | Rohde et al. |
| 6,002,036 | A | 12/1999 | Kadokura |
| 2002/0161253 | A1 * | 10/2002 | Voll et al. .................. 556/143 |

OTHER PUBLICATIONS

Journal Chemical Society. Dalton, Vol'kenau et al., (1980), 1961–1964.
Journal of Organometallic Chemistry, Pertici et al., 288 (1985), 341–348.

* cited by examiner

*Primary Examiner*—Porfirio Nazario-Gonzalez
(74) *Attorney, Agent, or Firm*—Rothwell, Figg, Ernst & Manbeck, P.C.

(57) ABSTRACT

The present invention provides a method of manufacturing a bis(cyclopentadienyl)ruthenium, comprising the step of synthesizing a bis(cyclopentadienyl)ruthenium by causing cyclopentadiene, ruthenium chloride and zinc powder to react in an alcohol solvent, wherein the synthesis of the bis(cyclopentadienyl)ruthenium comprises the step of mixing the cyclopentadiene and zinc powder in the alcohol solvent and thereafter adding ruthenium chloride portionwise while holding the temperature of the reaction system at from −70° C. to 20° C. A highly pure product can be obtained through purification of subliming bis(cyclopentadienyl)ruthenium having been synthesized in the synthesis step in an atmosphere under reduced pressure.

4 Claims, 2 Drawing Sheets

METHOD OF MANUFACTURING BIS (CYCLOPENTADIENLY)RUTHENIUM AND BIS(CYCLOPENTADIENYL)RUTHENIUM MANUFACTURED BY THE SAME

CROSS REFERENCE TO RELATED APPLICATION

This application is a 35 USC §371 National Phase Entry Application from PCT/JP03/09860, filed Aug. 4, 2003, and designating the U.S., which claims priority of JP 2002-227084 filed Aug. 5, 2002.

TECHNICAL FIELD

The present invention relates to a method of manufacturing a bis(cyclopentadienyl)ruthenium useful as a raw material for various types of organic ruthenium compounds.

BACKGROUND ART

In recent years, precious metal thin films of ruthenium, platinum, iridium, etc. or oxide films of these precious metals have been used as electrode materials of electrical and electronic parts, such as capacitors of ICs and LSIs. This is because they have especially excellent electrode characteristics when these precious metals are formed as thin film electrodes, and in particular, ruthenium and ruthenium oxides are receiving attention because they are considered to become main materials for thin film electrodes in the future.

In addition to sputtering, the chemical vapor deposition method (hereinafter referred to as the CVD method) is used as methods of manufacturing ruthenium and ruthenium oxide thin films. This is because the CVD method makes it easy to manufacture uniform films and besides the CVD method is excellent in step coverage.

Among other metal compounds, organic metal compounds which have low melting points and are easy to handle are often used as raw materials used in the CVD method. A bis(cyclopentadienyl)ruthenium derivative is known as a CVD material for manufacturing ruthenium thin films.

The bis(cyclopentadienyl)ruthenium derivative is obtained by introducing a substituent, such as an alkyl group, an acetyl group and a carbonyl group, in either or both of the cyclopentadienyl groups of bis (cyclopentadienyl)ruthenium. The reason why this bis (cyclopentadienyl)ruthenium derivative is useful as a CVD material is that, in addition to a high vapor pressure, this derivative has a low melting point and is in a liquid state at room temperature, with the result that this derivative is excellent in convenience in handling in the thin film manufacturing process. The reason why the bis(cyclopentadienyl) ruthenium derivative has such characteristics is that bis (cyclopentadienyl)ruthenium, which is the basic substance of this derivative, basically has properties which are desirable as a CVD raw material and because it is possible further lower the melting point and the steam pressure by introducing a prescribed substituent.

Although as described above, bis(cyclopentadienyl) ruthenium itself is useful as a CVD material, it can be thought that in the future bis(cyclopentadienyl)ruthenium will be more valuable as a material for manufacturing bis(cyclopentadienyl)ruthenium derivatives.

There is known a method of manufacturing a bis (cyclopentadienyl)ruthenium which involves synthesizing a bis(cyclopentadienyl)ruthenium by causing ruthenium chloride, cyclopentadiene and zinc powder to react in an alcohol solvent, removing trace amounts of impurities by use of column chromatography etc. and thereafter purifying the bis(cyclopentadienyl)ruthenium through recrystallization in an organic solvent (for the details of the above manufacturing method, refer to Journal Chemical Society. Dalton, (1980), 1961–1964 and Journal of Organometallic Chemistry, 288 (1985), 341–348). The reason why in this synthesis method, zinc is caused to be present in a reaction system is that zinc has a catalytic action to the synthetic reaction of bis(cyclopentadienyl)ruthenium.

However, this publicly known conventional method had the problem that the yield (percentage to the ruthenium chloride as a raw material, in terms of molar ratio) of manufactured bis(cyclopentadienyl)ruthenium is about 75%, a relatively low value. Furthermore, the above-described purification by recrystallization not only requires a large amount of solvent, raising the cost of manufacturing, but also makes it difficult to recover ruthenium which is lost in the solvent during the purification step. In addition, in the conventional method nonvolatile impurities sometimes got mixed in refined ruthenium, though in trace amounts.

The present invention was made against the above-described background and has as its object the provision of a manufacturing method by which a high-purity bis (cyclopentadienyl)ruthenium can be manufactured at a high yield.

DISCLOSURE OF THE INVENTION

In order to solve the above-described problems, the present inventors devoted themselves to research. They first examined the order of reaction of each raw material (a solvent, cyclopentadiene, zinc powder, ruthenium chloride) during reactions and the distribution ratio of these raw materials in the manufacturing process of a bis (cyclopentadienyl)ruthenium.

In the conventional synthesis method of a bis (cyclopentadienyl)ruthenium, ruthenium chloride, cyclopentadiene and zinc powder are simultaneously mixed in an alcohol solvent or ruthenium chloride is first dissolved in an alcohol solvent and after that, cyclopentadiene and zinc powder are then mixed. And it is a general practice to mix all these raw materials in all amounts at a time.

In this conventional synthesis step, it was a general practice to mix the raw materials at a mixing ratio of ruthenium chloride, cyclopentadiene and zinc powder of 1:64:40 or so (molar ratio). The reaction ratio in this conventional method deviates greatly from the stoichiometric composition of an aimed-at bis(cyclopentadienyl) ruthenium and from the standpoint of the stoichiometric composition, the mixed amounts of the cyclopentadiene and the zinc powder are excessive. The reason why the mixing ratio of cyclopentadiene and zinc powder is set at a high value is that the synthesis reaction of a bis(cyclopentadienyl) ruthenium is positively caused to occur. That is, because in the conventional method, cyclopentadiene polymerizes during a reaction under the formation of dicyclopentadiene, the amount of cyclopentadiene which contributes to the reaction decreases and, therefore, it is necessary to consider the portion which decreases.

The present inventors considered that one of the causes of the low yield of a bis(cyclopentadienyl)ruthenium is that the mixing ratio of the raw materials in this synthesis method deviates greatly from the stoichiometric composition.

Bis(cyclopentadienyl)ruthenium is a solid substance at room temperature and insoluble in alcohols such as ethanol. Therefore, a synthesized bis(cyclopentadienyl)ruthenium precipitates as a deposit in an ethanol solvent. However, bis(cyclopentadienyl)ruthenium is soluble in cyclopentadiene. For this reason, part of the bis(cyclopentadienyl) ruthenium is dissolved in cyclopentadiene and this cyclopentadiene is dissolved in ethanol. Therefore, in the conventional manufacturing method, a reaction solution after a reaction is filtered and bis(cyclopentadienyl) ruthenium which precipitates is filtered off and, on the other hand, the bis(cyclopentadienyl)ruthenium is recrystallized by heating and concentrating a filtrate.

However, in concentrating this filtrate, the cyclopentadiene in the filtrate polymerizes due to heat under the formation of dicyclopentadiene. And the bis(cyclopentadienyl)ruthenium which has been dissolved in the cyclopentadiene is dissolved in the dicyclopentadiene as it is, whereas it is difficult to remove the dicyclopentadiene, which has a high boiling point of 170° C., by ordinary heating and concentration. For this reason, even if the filtrate is heated and concentrated, it is impossible to recover the bis(cyclopentadienyl)ruthenium which has been dissolved in the dicyclopentadiene and losses occur. It might be thought that the larger the amount of cyclopentadiene in a reaction system, the larger the losses will be, and it might be thought that this is the cause of decreased yields of bis(cyclopentadienyl)ruthenium in the conventional synthesis method.

On the basis of the above considerations, the present inventors considered that in order to ensure a high yield in the synthesis stage of a bis(cyclopentadienyl)ruthenium, it is necessary to reduce the mixed amounts of cyclopentadiene and zinc thereby to make the mixed ratio of the raw materials close to a stoichiometric composition as far as possible. And they thought that, for this purpose, it is necessary to suppress the polymerization reaction of cyclopentadiene in the process of synthesis thereby to ensure that the synthesis reaction proceeds without causing the lack of cyclopentadiene to occur.

The polymerization reaction of cyclopentadiene can be suppressed by setting the temperature of the reaction system at a temperature not higher than room temperature. That is, the temperature of the reaction system is kept at a low level by cooling the reaction system in the synthesis step. According to the present inventors, it is desirable that the temperature of the reaction system be −70° C. to 20° C. and it is more desirable that the temperature of the reaction system be −60° C. to −10° C.

On the other hand, even if the reaction system is kept at a low temperature, it is also necessary to consider a temperature rise by the heat of reaction. This is because the synthesis reaction of a bis(cyclopentadienyl)ruthenium is an exothermic reaction and hence if the raw materials are mixed at a time as in the conventional method, the synthesis reaction proceeds at a stretch and abrupt heat generation occurs. Therefore, even if the reaction system is held at the above-described temperature, the temperature of the reaction system becomes not less than room temperature due to the heat of reaction and the polymerization of cyclopentadiene occurs, with the result that cyclopentadiene may become insufficient.

Hence, the present inventors considered that in order to suppress such an abrupt rise of the temperature of the reaction system, it is desirable that the synthesis reaction of a bis(cyclopentadienyl)ruthenium proceed as gently as possible. They thought that as a technique it is appropriate to change the reaction order of the raw materials. That is, cyclopentadiene and zinc powder are first mixed and after that, ruthenium chloride is added portionwise. By adopting this technique, the synthesis reaction of a bis(cyclopentadienyl)ruthenium proceeds each time ruthenium chloride is added. Therefore, it becomes possible to control the synthesis reaction and to suppress the overheating of the reaction system.

And on the basis of the above considerations the present inventors hit upon a method by which a bis(cyclopentadienyl)ruthenium is synthesized at a high yield.

That is, the method of manufacturing a bis(cyclopentadienyl)ruthenium related to the present invention is a method of manufacturing a bis(cyclopentadienyl)ruthenium which includes the step of synthesizing a bis(cyclopentadienyl)ruthenium by causing cyclopentadiene, ruthenium chloride and zinc powder to react in an alcohol solvent, which is characterized in that the synthesis of the bis(cyclopentadienyl)ruthenium is the step of mixing the cyclopentadiene and zinc powder in the alcohol solvent and thereafter adding ruthenium chloride portionwise, and that the reaction is carried out with the reaction system-held in the temperature range from −70° C. to 20° C.

According to the present invention, even if the mixing ratio of the raw materials of ruthenium chloride, cyclopentadiene and zinc powder is made close to a stoichiometric composition, it is possible to ensure that the raw materials react completely without excess or deficiency of each raw material. This is because the polymerization of cyclopentadiene can be suppressed by holding the reaction system at a low temperature, with the result that a formed bis(cyclopentadienyl)ruthenium can be prevented from being dissolved in cyclopentadiene which might polymerize. Furthermore, this is because adding ruthenium chloride portionwise prevents the synthesis reaction of a bis(cyclopentadienyl)ruthenium from proceeding abruptly, thereby to prevent the overheating of the reaction system. And by ensuring that each raw material reacts neither too much nor too less, it is possible to improve the yield of a bis(cyclopentadienyl)ruthenium.

Although in the present invention it is possible to make the ratio (molar ratio) of ruthenium chloride, cyclopentadiene and zinc powder which are mixed for the synthesis of a bis(cyclopentadienyl)ruthenium closer to a stoichiometric composition, in order to ensure a high yield of the bis(cyclopentadienyl)ruthenium it is preferred that the mixing ratio of ruthenium chloride, cyclopentadiene and zinc powder in the invention be 1:3:2 to 1:10:3.

The reason why ruthenium chloride is selected as a raw material to be added portionwise in the invention is that if added amounts of raw materials are mistaken even a little in ensuring that the synthesis reaction of a bis(cyclopentadienyl)ruthenium proceeds, the reaction would proceeds abruptly and the reaction system might be overheated. In this case, unlike zinc, ruthenium chloride can be added in a solution state and it is possible to add an accurate amount of ruthenium chloride.

This ruthenium chloride may be added in a hydrate state and also its form may be a trihydrate or a mixture of a monohydrate to a trihydrate. Although ruthenium chloride in a solid state (a powder state) may be added, it is desirable to add ruthenium chloride by dissolving the ruthenium chloride in an alcohol and adding this solution dropwise. That is, it is preferred that a ruthenium chloride-alcohol solution in which ruthenium chloride is dissolved in an alcohol be prepared in a step separate from the step of mixing cyclopentadiene and zinc powder in an alcohol solvent and that this solution be added to the reaction system. This is because in the case of ruthenium chloride in a solution state, it is easy to control the ruthenium chloride concentration in the reaction system and hence the reaction rate can be kept constant, with the result that the formation reaction of a bis(cyclopentadienyl)ruthenium becomes gentle and a side reaction is suppressed.

In adding ruthenium chloride in a solution state portionwise, it is preferred that the ruthenium chloride concentration of the ruthenium chloride-alcohol solution be 0.1 to 4 mol/l and that the ruthenium chloride-alcohol solution be added at an addition rate of 500 to 1000 ml/h. This is because according to the present inventors have found that adjustment of the conditions within these ranges prevents the reaction system from overheating and allows ruthenium chloride added to be completely consumed in the reaction to produce bis(cyclopentadienyl)ruthenium.

Incidentally, for the zinc powder which is another raw material, it is desirable that the zinc powder have a particle size which permits easy suspension in a solvent and that the particle size be not less than 200 meshes or so. Incidentally, although the type of alcohol which is a solvent is not especially limited, it is desirable to use ethyl alcohol. Furthermore, because the object of the present invention is to manufacture a high-purity bis(cyclopentadienyl)ruthenium, both the zinc powder and the cyclopentadiene which are to be used should have a high purity.

Although by the above-described synthesis method of a bis(cyclopentadienyl)ruthenium it is possible to manufacture a bis(cyclopentadienyl)ruthenium at a high yield in the synthesis step, the purification step is necessary because the manufactured bis(cyclopentadienyl)ruthenium is often inferior in purity if there is no purification step. The purification step is an important step because it influences a final yield.

The present inventors examined a more efficient purification method which is to replace the conventional purification step based on the recrystallization method. As a result, they reached the conclusion that it is desirable to refine a synthesized bis(cyclopentadienyl)ruthenium by the sublimation method. In purification by the sublimation method, a solid bis(cyclopentadienyl)ruthenium manufactured in the synthesis step is heated and the bis(cyclopentadienyl)ruthenium is vaporized and recovered. This sublimation method utilizes the relatively high vapor pressure of a bis(cyclopentadienyl)ruthenium and by applying the sublimation method it is possible to avoid the contamination with nonvolatile impurities and to refine a high-purity bis(cyclopentadienyl)ruthenium. Furthermore, the purification by this sublimation method is a relatively simple step which involves collecting solid matter from a reaction solution after the synthesis step by performing filtration etc. and heating this solid matter, and it provides the advantage that purification can be preformed with fewer steps than in the conventional method.

And it is preferred that this purification by the sublimation method be performed in an atmosphere under reduced pressure. Bis(cyclopentadienyl)ruthenium has a low vaporizing rate at an atmospheric pressure although its vapor pressure is relatively high and hence it takes time to recover bis(cyclopentadienyl)ruthenium. Therefore, by subliming a synthesized bis(cyclopentadienyl)ruthenium under reduced pressure, it is possible to recover an efficiently refined bis(cyclopentadienyl)ruthenium.

In this purification step, a reaction solution obtained in the synthesis step is filtered or concentrated and dried, thereby to separate a sold reactant, and this solid reactant is heated. It is preferred that the heating temperature at this time be 100 to 120° C. Furthermore, it is preferred that the pressure in a case where heating is performed in an atmosphere under reduced pressure be 3 to 100 Pa. And by recovering and cooling a bis(cyclopentadienyl)ruthenium which vaporizes by this heating, it is possible to obtain a solid bis(cyclopentadienyl)ruthenium. Incidentally, it is preferred that the solid reactant separated from the reaction solution be rinsed before the sublimation.

By passing through the above-described synthesis step and purification step, it is possible to efficiently manufacture a high-quality bis(cyclopentadienyl)ruthenium. According to the present inventors, by a method of manufacturing a bis(ethylcyclopentadienyl)ruthenium related to the invention, it is possible to manufacture a bis(cyclopentadienyl)ruthenium at a high yield of not less than 95%. A bis(cyclopentadienyl)ruthenium manufactured by the invention is a high-purity organic ruthenium compound which does not contain impurities, such as nonvolatile substances, which might have contaminated a bis(cyclopentadienyl)ruthenium in the conventional method.

Incidentally, a bis(cyclopentadienyl)ruthenium itself which is manufactured by the present invention is suitable as a CVD raw material due to its high purity. However, by introducing various types of substituent, it is possible to manufacture compounds which are more desirable as CVD raw materials. For example, it is bis(ethyl cyclopentadienyl)ruthenium that has been receiving attention in recent years as a raw material for the manufacturing of ruthenium or ruthenium oxide thin films by the CVD method. This bis(ethyl cyclopentadienyl)ruthenium can be manufactured by introducing an ethyl group in a bis(cyclopentadienyl)ruthenium manufactured by the present invention.

BEST MODE FOR CARRYING OUT THE INVENTION

A preferred embodiment of the invention and a comparative example will be described below.

In this embodiment, a bis(ethyl cyclopentadienyl)ruthenium was produced by use of ethyl cyclopentadiene as cyclopentadiene.

In a separable flask, 528 g (8 moles) of cyclopentadiene and 130 g (2 moles) of zinc powder of 200 meshes were put in 1500 ml of ethyl alcohol as an alcohol solvent, cooled to −60° C. and mixed by stirring. On the other hand, in a step separate from this step, a ruthenium chloride solution was prepared by dissolving 262 g (1 mole) of ruthenium chloride trihydrate ($RuCl_3.3H_2O$) in 500 ml of ethyl alcohol at room temperature. And the ruthenium chloride solution was added dropwise at a rate of 250 ml/l (one drop/hour) for 2 hours during stirring, with the temperature of a mixed solution of ethyl cyclopentadiene and zinc powder kept at not more than −10° C. Because an intense exothermic reaction occurs during the dropwise addition of the ruthenium chloride solution, care should be used so that the solution temperature does not exceed −10° C. during the dropwise addition of the solution. And after all the solution was added dropwise, a reaction was caused to occur for 24 hours with the solution temperature kept at 10° C. The mixing ratio of the raw materials on this occasion was ruthenium chloride: cyclopentadiene: zinc=1:8:2.

After the reaction, it was ascertained that the solution discolored from blue to reddish brown and then the reaction solution was filtered. On this occasion, the zinc powder and the greater part of a synthesized bis(cyclopentadienyl) ruthenium are separated on filter paper. On the other hand, the bis(cyclopentadienyl)ruthenium is dissolved in the filtrate, though in small amount. Therefore, the filtrate was concentrated with an evaporator at 60° C. and at $1.3 \times 10^4$ Pa and then refiltered. Solid left after filtration obtained by this refiltration were rinsed with 500 ml of ethanol to remove organic impurities and further rinsed with 500 ml of water to remove inorganic impurities. These solid left after filtration were collected and dried at 25° C. under reduced pressure at $1.3 \times 10^2$ Pa.

Figure 1:
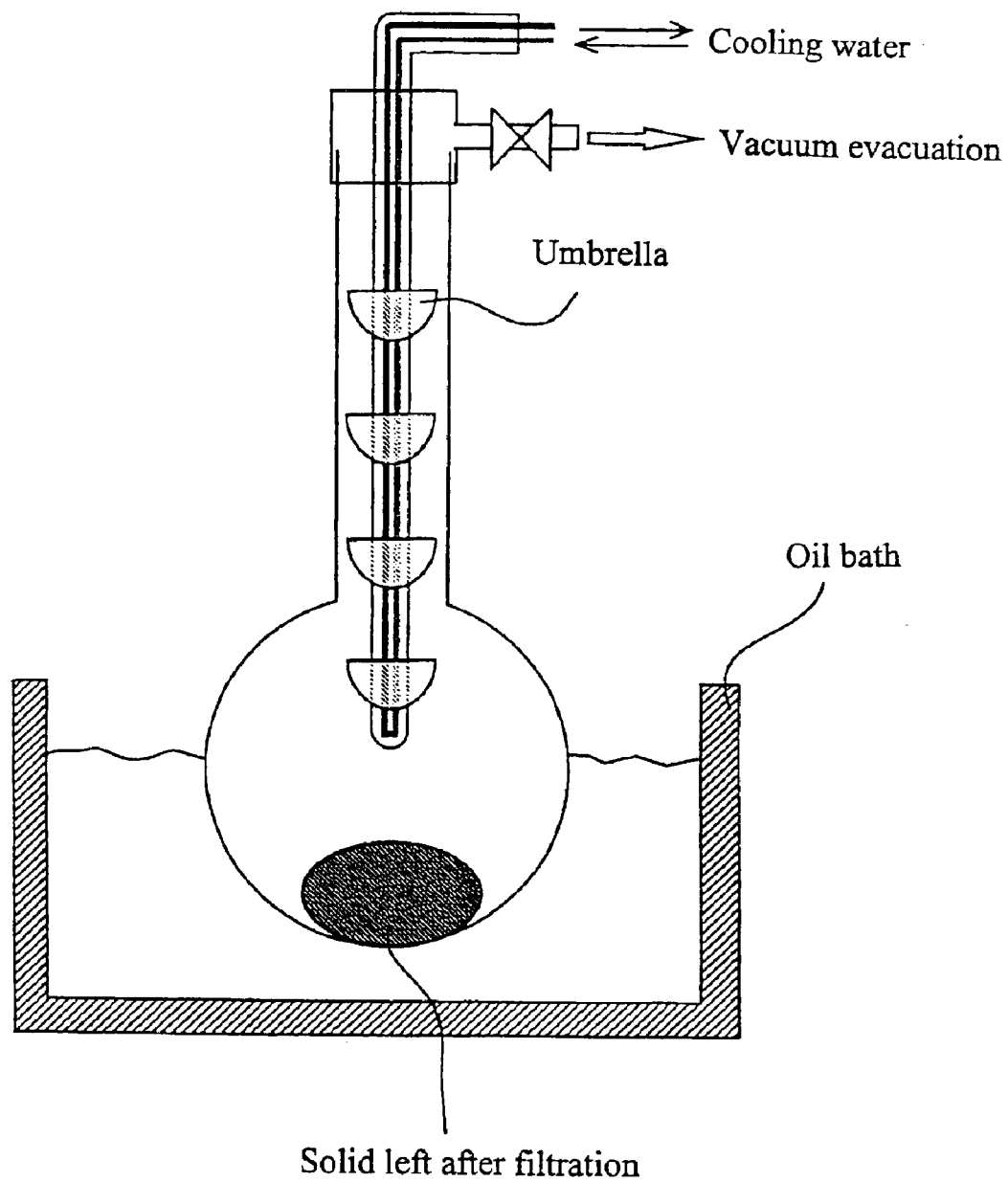
FIG. 1 is a schematic view showing the construction of a sublimation apparatus used in this embodiment.
Figure 2:
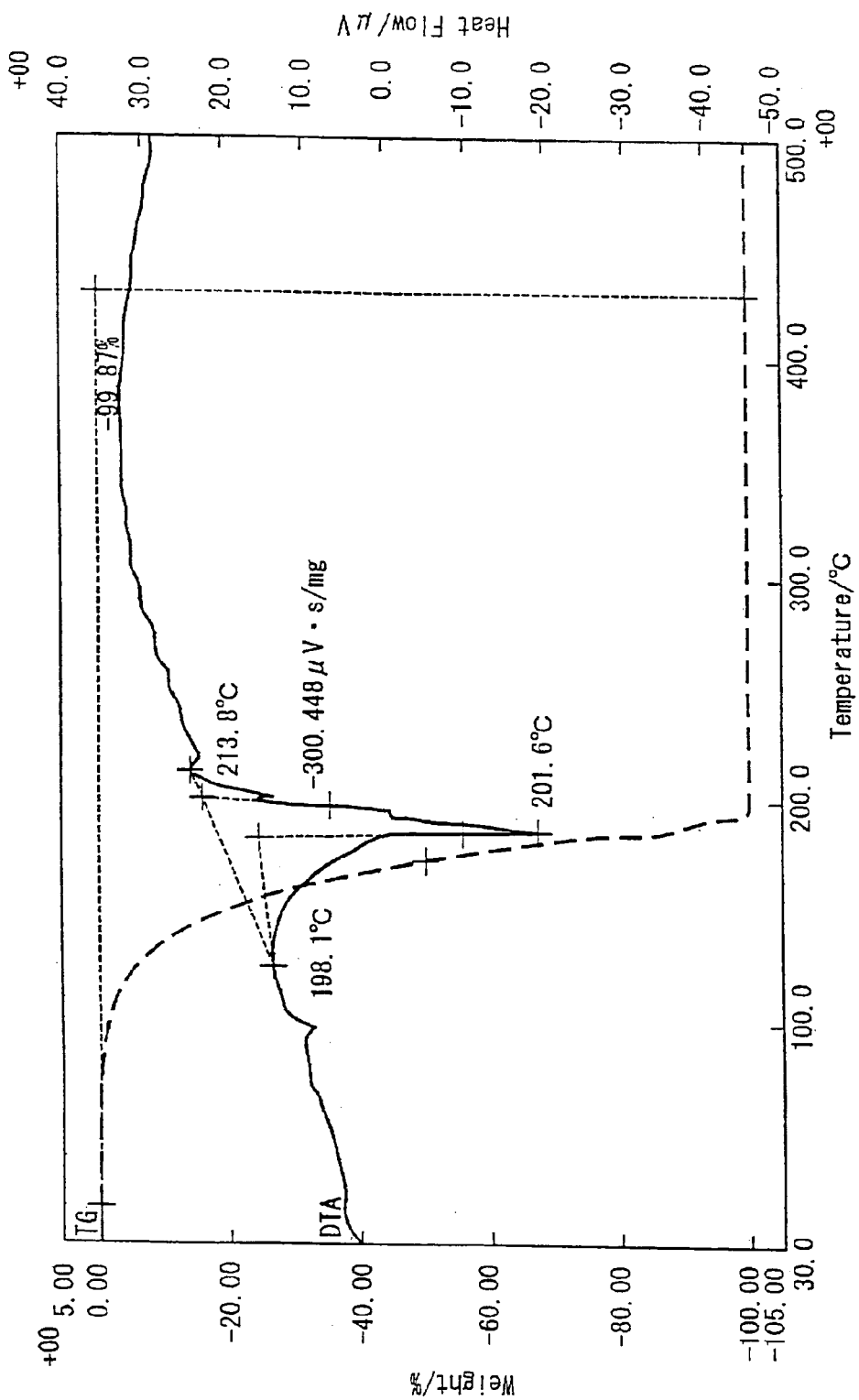
FIG. 2 is a TG/DTA curve of a bis(cyclopentadienyl)ruthenium manufactured in this embodiment.

The dried solid left after filtration was refined under reduced pressure by the sublimation method. This purification step was performed by use of a sublimation apparatus as shown in FIG. 1. In this sublimation apparatus, the solid left after filtration (constituted by a bis(cyclopentadienyl) ruthenium, zinc powder, nonvolatile impurities, etc.) on the bottom of a flask under reduced pressure is heated in an oil bath thereby to sublime the bis(cyclopentadienyl)ruthenium. In order that the sublimed bis(cyclopentadienyl)ruthenium is cooled by water-cooled umbrellas and recrystallizes, the umbrellas are taken out and the adhering bis (cyclopentadienyl)ruthenium is recovered. For the purification conditions used, the heating temperature was 110° C. and the pressure was 13.3 Pa. The amount of the bis (cyclopentadienyl)ruthenium produced at that time was 220 g and the yield was 95%. When the bis(cyclopentadienyl) ruthenium produced in this embodiment was analyzed by TG/DTA (thermogravimetric/differential thermal analysis), results as shown in FIG. 2 were obtained. From the analysis results it was ascertained that the bis(cyclopentadienyl) ruthenium produced in this embodiment has a purity of 99.99% and does not contain nonvolatile impurities.

Comparative Example

In order to verify the purity of the bis(cyclopentadienyl) ruthenium produced in this embodiment, a bis (cyclopentadienyl)ruthenium was produced by a conventional method.

In a flask in which the atmosphere had been replaced with nitrogen, 119.6 g (0.457 mole) of ruthenium chloride was dissolved in 2500 ml of ethyl alcohol and then 1158 g (17.55 moles) of cyclopentadiene and 163 g (2.49 moles) of zinc powder were added to this solution at a time. And this mixed solution was stirred at room temperature for 1 hour and a reaction was caused to occur. A deposit after the reaction was filtered and hot toluene was caused to pass through filter paper. Next, a filtrate was concentrated to 500 ml under reduced pressure by use of a rotary evaporator and the concentrate was caused to pass through an alumina column by using hexane and ethyl acetate as solvents, whereby a bis(cyclopentadienyl)ruthenium was separated. The separated liquid was concentrated by use of a rotary evaporator and the concentrate was dried at 25° C. in a vacuum of $1.3 \times 10^2$ Pa, whereby bis(ethyl cyclopentadienyl)ruthenium was obtained. The amount of the bis(cyclopentadienyl) ruthenium produced at that time was 84.36 g and the yield was 73.5.

When this produced bis(ethyl cyclopentadienyl) ruthenium was analyzed, it was found that its purity was 94.5%—a low purity.

INDUSTRIAL APPLICABILITY

As described above, according to the present invention, it is possible to manufacture a high-purity bis (cyclopentadienyl)ruthenium at a higher yield than previously. Although it is possible to use the bis (cyclopentadienyl)ruthenium itself which is manufactured by the invention as a CVD raw material, it can be used as a raw material for manufacturing organic ruthenium compounds which are more suitable as a material for a bis(ethyl cyclopentadienyl)ruthenium etc.

What is claimed is:

1. A method of manufacturing a bis(cyclopentadienyl) ruthenium, comprising the step of synthesizing a bis (cyclopentadienyl)rutheniun by causing a cyclopentadiene, ruthenium chloride and zinc powder to react in an alcohol solvent, wherein the synthesis of the bis(cyclopentadienyl) ruthenium comprises the step of mixing the cyclopentadiene and zinc powder in the alcohol solvent and thereafter adding the ruthenium chloride portionwise, and the reaction is carried out with the reaction system held in the temperature range from −70° C. to 20° C.

2. The method of manufacturing a bis(cyclopentadienyl) ruthenium according to claim 1, wherein the mixing ratio of the cyclopentadiene, ruthenium chloride and zinc powder is from 3:1:2 to 10:1:3 in terms of molar ratio.

3. The method of manufacturing a bis(cyclopentadienyl) ruthenium according to claim 1, wherein ruthenium chloride is added portionwise by dropwise addition of a ruthenium chloride-alcohol solution.

4. The method of manufacturing a bis(cyclopentadienyl) ruthenium according to claim 1, wherein the method includes the purification step of subliming the bis (cyclopentadienyl)ruthenium having been synthesized in the synthesis step in an atmosphere under reduced pressure.

* * * * *

UNITED STATES PATENT AND TRADEMARK OFFICE
CERTIFICATE OF CORRECTION

PATENT NO.         : 7,012,150 B2                                         Page 1 of 1
APPLICATION NO. : 10/491125
DATED              : March 14, 2006
INVENTOR(S)        : Takeyuki Sagae It is certified that error appears in the above-identified patent and that said Letters Patent is hereby corrected as shown below:

On the title page: item should read
(54) METHOD OF MANUFACTURING BIS (CYCLOPENTADIENYL) RUTHENIUM AND BIS (CYCLOPENTADIENYL) RUTHENIUM MANUFACTURED BY THE SAME Signed and Sealed this First Day of August, 2006

JON W. DUDAS
*Director of the United States Patent and Trademark Office*